(12) United States Patent
Backstrom et al.

(10) Patent No.: US 6,455,516 B1
(45) Date of Patent: Sep. 24, 2002

(54) METHOD AND COMPOUNDS FOR USE IN THE TREATMENT OF STEROID INDUCED STATES OF THE CENTRAL NERVOUS SYSTEM

(76) Inventors: Torbjorn Backstrom, Sofiehemsvagen 73 A, S-907 38, Umea (SE); Ming-De Wang, KarnVagen 123, S-906 27, Umea (SE)

( * ) Notice: Subject to any disclaimer, the term of this patent is extended or adjusted under 35 U.S.C. 154(b) by 0 days.

(21) Appl. No.: 09/266,035

(22) Filed: Mar. 11, 1999

Related U.S. Application Data (63) Continuation-in-part of application No. 09/037,869, filed on Mar. 11, 1998, now abandoned.

(51) Int. Cl.$^7$ ............................................... A01N 45/00
(52) U.S. Cl. ................................................... 514/169
(58) Field of Search ............................. 514/169–172, 514/176, 177, 178, 179, 180, 181, 182; 540/94–99, 106–112, 114, 116, 36; 552/600, 540–542, 544, 546, 547, 505, 640–641, 647–649

(56) References Cited

U.S. PATENT DOCUMENTS

| | | | |
|---|---|---|---|
| 5,120,723 A | | 6/1992 | Gee et al. |
| 5,232,917 A | * | 8/1993 | Bolger et al. ............... 514/176 |
| 5,939,545 A | * | 8/1999 | Upasani et al. |

FOREIGN PATENT DOCUMENTS

| | | |
|---|---|---|
| WO | WO9505826 | 3/1995 |
| WO | WO9616076 | 5/1996 |
| WO | WO9850042 | 11/1998 |

OTHER PUBLICATIONS

Kokate et al., Neuropharmacology, 35 (8) 1049–56., 1996.*
Kokate et al., J. of Pharm. And Exptl. Ther., vol. 270, No. 3, pp. 1223–1229 (abstract)., 1994.*
Lan et al., J. of Neurochemistry, pp. 1818–1821., 1991.*
Serra et al., J. of Neurochemistry, vol. 75, No. 2, pp. 732–740., 2000.*
Snead, Annal. of Neurology, pp. 688–691., 1998.*
Backstrom et al,, Mood Disorders in Woman, eds. Steiner et al., London: Martin Dunitz Ltd., pp. 189–205., 2000.*
Backstrom et al., Epilepsy: A Comprehensive Textbook, Chapter 189: Effect of Hormones on Seizure Expression, eds.: J. Engel Jr. Lippincott–Raven Publishers: Philadelphia, pp. 2003–2012., 1997.*
Prince et al., *Neuropharmacology*, vol. 32, No. 1, pp. 59–63 (1993).
Chen et al., *Pharmacol., Biochem. Behav.*, vol. 53, No. 4, pp. 777–782 (1996) (Abstract).
Zimmerman et al., *Pharmacol., Biochem. Behav.*, vol. 47, No. 3, pp. 735–738 (1994) (Abstract).
Holzbauer, *Brit. J. Pharmacol.*, vol. 43, No. 3, pp. 560–569 (1971) (Abstract).
Holzbauer, *J. Physiol.*, vol. 215, No. 1, p. 16 (1971) (Abstract).
Rembihsa et al., Experientia, vol. 30, No. 1 (1974) pp. 82–83.
Pince et al., Neuropharmacology, vol. 32, No. 1 (1993) pp. 59–63, XP002110081.
Gonzalez–Mariscal et al., Neuroendocinology, vol. 34 (1982) pp. 357–362 XP002110082.

* cited by examiner

*Primary Examiner*—Ralph Gitomer
(74) *Attorney, Agent, or Firm*—Birch, Stewart, Kolasch & Birch, LLP.

(57) ABSTRACT

The use of epiallopregnanolone (3β-hydroxy-5α-pregnan-20-one) for the treatment of steroid induced mood disorders and CNS disorders is disclosed. Further, the use of epiallopregnanolone for the manufacture of pharmaceuticals is disclosed, together with an list of symptoms suitable for treatment with epiallopregnanolone.

4 Claims, 5 Drawing Sheets

METHOD AND COMPOUNDS FOR USE IN THE TREATMENT OF STEROID INDUCED STATES OF THE CENTRAL NERVOUS SYSTEM

This application is a continuation-in-part of application Ser. No. 09/037,869 filed on Mar. 11, 1998, now abandoned the entire contents of which are hereby incorporated by reference.

The present invention concerns the treatment of steroid induced mood disorders and disorders of the central nervous system (CNS) and in particular new pharmaceuticals for this purpose.

The progesterone metabolites known as pregnanolones have been the subject of various studies, at least partially elucidating their role in the neurological signal system in mammals. The nomenclature differs somewhat in the field, but the pregnanolone group is generally considered to encompass the following compounds: 3alpha-hydroxy-5alpha-pregnan-20-one(allopregnanolone), 3alpha-hydroxy-5beta-pregnan-20-one (pregnanolone), 3beta-hydroxy-5alpha-pregnan-20-one (epiallopregnanolone), and 3beta-hydroxy-5-beta-pregnan-20-one (epipregnanolone).

TABLE 1

Nomenclature of the pregnanolone group

| IUPAC-nomenclature | Generic nomenclature |
|---|---|
| 3α-OH-5β-pregnan-20-one | allopregnanolone |
| 3α-OH-5β-pregnan-20-one | pregnanolone |
| 3α-OH-5α-pregnan-21-ol-20-one | allotetrahydrodeoxy corticosterone |
| 3α-OH-5β-pregnan-21-ol-20-one | tetrahydrodeoxy corticosterone |
| 3β-OH-5α-pregnan-20-one | epiallopregnanolone |
| 3β-OH-5β-pregnan-20-one | epipregnanolone |

3alpha-hydroxy-5alpha-pregnan-20-one is an important specific GABA-A {γ-aminobutyric acid (A)} receptor enhancer. It has a specific binding site located on the alpha- and/or beta-unit of the GABA-A receptor. It acts by enhancing the effect of GABA on the opening frequency of the GABA-A receptor and the opening duration. It has an effect similar both to benzodiazepines and barbiturates but has a binding site separate from both these compounds. The effect is specific on the GABA-A receptor and can be blocked by the GABA-antagonist picrotoxin. 3alpha-hydroxy-5alpha-prenan-20-one has a CNS-depressing effect and it is possible to induce anaesthesia with a high pharmacological dose. It can also be used as anti-epileptic substance, sleeping-pill and as anti-migraine effect. It has also shown anxiolytic effects in animal experiments. All this in high concentrations and in high doses.

3alpha-hydroxy-5beta-pregnan-20-one, 3alpha-hydroxy-5alpha-pregnan-21-ol-20-one and 3alpha-hydroxy-5beta-pregnan-21-ol-20-one have similar effects as the above-described steroid but are less potent. They have slightly different pharmacogenetic properties suggesting that there might be two binding sites for the steroids on the GABA-A receptor.

3beta-hydroxy-5alpha-pregnan-20-one: This progesterone metabolite is the steroid involved in the present invention, described in more detail below.

3beta-hydroxy-5beta-pregnan-20-one: This steroid seems to have no effect either as a blocker or as an antagonist to the above sedative steroids. The present inventors have also tested 3beta-hydroxy-pregnanolone which is a steroid having a double-bond between the 4th and 5th coal atom and no 5-reduction. This steroid has no effect either as an agonist or blocker or antagonist. Obviously, the pregnanolones in spite of their structural similarities, have highly differing modes of action, if any, in the mammal neurochemical environment.

Steroid induced mood disorders are a frequent problem among women and in particular during the luteal phase of the menstrual cycle. Associated to this, some oral contraceptives have shown to have an negative influence on the CNS, such as mood disorders. Further, many other CNS disorders are believed to be steroid induced. Finally, the development of steroid based anesthetics require the availability of effective anti-anaesthetics.

PRIOR ART

Prince and Simmons (*Neuropharmacology*, vol. 32, no. 1, pp. 59–63, 1993) have used a model of membrane fractions of whole male rat brain. In this sub-fraction of whole brain homogenate they have used the binding of a benzodiazepine, 3H-flunitrazepam, as a model for steroid effect and change of GABA-A receptor conformation. This test has been suggested as an indicator of allosteric modulation of the GABA-A receptor. The relationship between the change in flunitrazepam (FNZ) binding and change in chloride flow at GABA-stimulation is uncertain and a change in binding can not be taken as a proof of change in chloride flow through the GABA-receptor or change in GABA-A receptor function. The change in chloride flow is the important effect.

The central question, if there exists a relationship between change in FNZ-binding and neuronal excitability is even less clear and such conclusions can not be drawn from results on FNZ-binding. A change in FNZ-binding properties or absence of such change in binding properties does not imply a change or absence of change in neural activity or GABA-A mediated chloride flow.

It is also well known that the GABA-A receptor contains several sub-units that can be combined in multiple ways. It is known that certain combinations lack steroid recognition site. It is also known that the effect of steroid on the binding of a convulsant substance TBPS differs in different brain regions. Further, it is known that the binding of TBPS varies with the estrus cycle in female rats indicating an effect change related to the ovarian hormone production. These changes related to estrus cycle can not be noticed in male rats used in the studies of Prince and Simmons (supra).

There is no indication in the prior art that 3beta-hydroxy-5alpha-pregnan-20-one by itself causes any measurable CNS-activity changes in vitro or in vivo. On the contrary, the findings are in fact contradictory.

SUMMARY OF THE INVENTION

The present invention discloses for the first time a practical use of 3beta-hydroxy-5alpha-pregnan-20-one as a pharmaceutical inter alia for the treatment of steroid induced CNS disorders, mood disorders, memory disorders and for use as an anti-anaestheticum and antisedativum, according to the attached claims.

SHORT DESCRIPTION OF THE FIGURES

The invention will be described in closer detail in the following, with reference to the attached drawings, in which.

DESCRIPTION OF THE INVENTION

The present invention focuses on 3beta-hydroxy-5alpha-pregnan-20-one. This steroid has been shown, by the present inventors, to be an antagonist and that it can block the effect of 3alpha-hydroxy-5alpha-pregnan-20-one and 3alpha-hydroxy-5beta-pregnan-20-one in vivo. The blocking effect was also demonstrated in vitro. Surprisingly, simultaneous treatment with 3beta-hydroxy-5alpha-pregnan-20-one inhibits in vivo the CNS depressing effect of 3alpha-hydroxy-5alpha-pregnan-20-one. 3beta-hydroxy-5alpha-pregnan-20-one has no effect by itself on the GABA-A receptor and has hitherto, according to available literature, not been shown to have any effect in in vitro experiments or in in vivo experiments by itself. The effect is thus to block and antagonize the effects of the sedative 3alpha-hydroxy-5alpha-pregnan-20-one and 3alpha-hydroxy-5beta-pregnan-20-one.

It can thus be concluded, that 3beta-hydroxy-5alpha-pregnan-20-one is specific in its effect as a blocker of steroid-induced sedation. This is a surprising finding, underlying the present invention.

Analogues to 3beta-hydroxy-5alpha-pregnan-20-one can be made by preserving the relationship between the 3beta and 5alpha structures. A pre-drug to this steroid could be 5alpha-reduced steroids with a sulphate group at 3 position. They would easily be converted to 3beta-hydroxy steroids in the body. An ethanyl group at the 17 position of the steroid molecule will also increase the bio-availability of such a steroid.

To be able to discover if a certain steroid has an agonistic or antagnositic effect or if it could be used as a therapeutic substance one has to show that it can block, in vivo, a general CNS-function induced by the steroid to be blocked.

3beta-hydroxy-5alpha-pregnan-20-one has been shown by the present inventors to inhibit the effect of 3alpha-hydroxy-5alpha-pregnan-20-one and 3alpha-hydroxy-5beta-pregnan-20-one in rats. It has also been shown that 3alpha-hydroxy-5alpha-pregnan-20-one is higher in the brain from women who died in the luteal phase compared to matched postmenopausal women. 3alpha-hydroxy-5alpha-pregnan-20-one and 3alpha-hydroxy-5beta-pregnan-20-one are also higher in plasma during the luteal phase than in the follicular phase. The luteal phase is the crucial phase of the ovarian cycle in humans for presence of negative mood, memory changes in premenstrual syndrome and changes in epileptic seizures in certain women with epilepsy.

By studying the FNZ-binding one can not assume that the same effect will be seen in a neural activity in vivo. This has also not been claimed by Prince and Simmons in their paper (supra). They have only discussed implications for binding sites of steroids and if they are the same or not. This is not a new discussion and the discussion of several binding sites for steroids has been indicated in other papers earlier. The only conclusion drawn by them and the possible conclusions to be done by using their experimental design and the model is that the steroid changes the binding of FNZ differently and have some interactions on the FNZ-binding. No conclusion of effects on neural activity or on clinical implications can be drawn from the results of Prince and Simmons. Such results can however be drawn from in vivo findings in rats, reported by the present inventors.

The results by Prince and Simmons are also different from the present in vitro results concerning the blocking or inhibiting effect of 3beta-hydroxy-5alpha-pregnan-20-one and 3beta-hydroxy-5beta-pregnan-20-one on 3alpha-hydroxy-5alpha-pregnan-20-one and 3alpha-hydroxy-5beta-pregnan-20-one effects in hippocampus.

A possible mechanism of action of 3beta-hydroxy-5alpha-pregnan-20-one in treatment of premenstrual syndrome would be to inhibit a down regulation of GABA-A receptor and thus keep up the sensitivity of the GABA-system and inhibit the development of a less sensitive state during the luteal phase. It has been shown in rat that there is a change of the GABA-A receptor during chronic progesterone treatment in rat. This will decrease the sensitivity for benzodiazepines, 3alpha-hydroxy-5alpha-pregnan-20-one and 3alpha-hydroxy-5beta-pregnan-20-one with a rebound effect after progesterone withdrawal. The effect was related to 3alpha-hydroxy-5alpha-pregnan-20-one concentration and the effect could be blocked by blocking the synthesis of 3alpha-hydroxy-5alpha-pregnan-20-one from progesterone. A similar situation was found in humans with premenstrual syndrome who have a decreased sensitivity in the GABA-A function during the luteal phase. One hypothesis is that the decreased sensitivity in the GABA-A system in PMS-patients is due to down-regulation of the GABA-A receptor made by 3alpha-hydroxy-5alpha-pregnan-20-one produced by the corpus luteum of the ovary. This down regulation may be hindered by an antagonist to 3alpha-hydroxy-5alpha-pregnan-20-one which 3beta-hydroxy-5alpha-pregnan-20-one is. In such situation 3beta-hydroxy-5alpha-pregnan-20-one is a treatment for premenstrual syndrome.

A compound according to the invention has the following formula (I):

where the substituents are as follows:
R1 is any one of —3βOH, —3βSO$_4$, and —NaO$_3$βSO
R2 is any one of —H, -methyl, -ethyl, -ethyl-ether, -2β-4-morholinyl, —CH$_3$CH$_2$O, and —CH$_3$CH$_2$CH$_2$O,
R3 is one of -Keto, —17β—OH, —COCH$_3$, —COCH$_2$Cl, —CHOHCH$_3$, —COH(CH$_3$)$_2$, —COCF$_3$, —CH$_2$COOH, —COCH$_2$OH—17β—OH, 17α-ethinyl, —COH$_2$CO-acetate, -16ene, —COH$_2$CO-hemisuccinate, —COH$_2$CO-methanesulfonate, —COH$_2$CO-phosphate-disodium salt, —COH$_2$CO-trimethylacetate, —COH$_2$CO-proprionate, and —COH$_2$CBr, R4 is one of —αH, and —βH, R5 is one of —17—OH, -ethynyl, -sulfoxyacetyl, -acetoxy, -methylene, benzoate, and —O-valerate, R6 is one of —H, -keto, —OH, -methyl, -ethyl, 11-alpha-dialkylamino, 11,18-Hemiacetal, —O-acetate, and —NaO$_3$SO, and R7 is one of H, —Cl, —F, —αCH$_3$, —βCH$_3$, and 6ethyl-ether.

The present invention concerns a method for the treatment and/or prevention of steroid induced mood disorders in human patients, according to which method 3beta-hydroxy-5alpha-pregnan-20-one is administered to said patient. Suitable routes of administration are for example the following: intravenously, nasally, per rectum, intravaginally, percutaneously and orally. Nasal administration in particular is a promising alternative, as it offers the benefits of ease and the possibility of self-administration by the patient. Percutaneous administration, using slow-release adhesive medicine patches, is another possible form of administration, similarly suitable for self-medication. In any of these routes of administration, special concern has to be given to the formulation of the composition, comprising the effective pharmaceutical in a chemical form, suitable for the chosen route, together with adjuvants and vehicles, conventionally used.

For the treatment of many CNS disorders and for the uses as an antianestheticum, it is however preferred that the effective compound is administered intravenously.

Suitable doses, according to the invention, in intravenous administration, are doses in the interval of 0.2–20 mg per kg body weight.

Further, the present invention encompasses a method for the treatment and/or prevention of CNS disorders in human patients, according to which method 3beta-hydroxy-5alpha-pregnan-20-one is administered to said patient. Examples of such disorders, believed to be steroid induced, include the following: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, Alzheimer's dementia, menstrual cycle linked difficulties in concentration, menstrual cycle linked sleep disorders and tiredness.

One preferred embodiment of the invention, addressing a problem afflicting numerous women, is a method for the treatment and/or prevention of side effects of postmenopausal therapy in human patients, according to which 3beta-hydroxy-5alpha-pregnan-20-one is administered to said patient.

Another preferred embodiment of the invention is the treatment and/or prevention of side effects of oral contraceptives in human patients, in which treatment 3beta-hydroxy-5alpha-pregnan-20-one is administered to said patient. In this application, it is preferred, that the effective composition 3beta-hydroxy-5alpha-pregnan-20-one is administered together with the oral contraceptive, taken by the patient. Nasal and percutaneous administration are also suitable routes of administration.

Further, the control and termination of steroid anaesthesia in human patients is suitable performed according to the invention in that 3beta-hydroxy-5alpha-pregnan-20-one is administered to said patient. Intravenous administration is the preferred route of administration, other routes can however be contemplated.

According to the present invention, tiredness in human patients can be treated and/or prevented by the administration of 3beta-hydroxy-5alpha-pregnan-20-one to said human patient.

Generally, the present invention discloses for the first time the use of 3beta-hydroxy-5alpha-pregnan-20-one as a therapeuticum and in particular the use of 3beta-hydroxy-5alpha-pregnan-20-one for the treatment of steroid induced mood disorders. Further, the invention encompasses the use 3beta-hydroxy-5alpha-pregnan-20-one for the treatment of CNS disorders.

One preferred embodiment is the use of 3beta-hydroxy-5alpha-pregnan-20-one for the treatment and prevention of side effects of post-menopausal therapy, as well as the use 3beta-hydroxy-5alpha-pregnan-20-one for the treatment and prevention of side effects of oral contraceptives.

The present invention discloses the use of 3beta-hydroxy-5alpha-pregnan-20-one for the treatment or prevention of any one of the following disorders: epilepsy, menstruation cycle dependent epilepsy, depression, stress related depression, migraine, tiredness and in particular stress related tiredness, premenstrual syndrome, premenstrual dysphoric disorder, menstrual cycle lined mood changes, menstrual cycle linked memory changes, stress related memory changes, Alzheimer's dementia, menstrual cycle linked difficulties in concentration, menstrual cycle linked sleep disorders and tiredness.

Consequently, the present invention encompasses the use of 3beta-hydroxy-5alpha-pregnan-20-one for the manufacture of a pharmaceutical for the treatment of steroid induced mood disorders, the use of 3beta-hydroxy-5alpha-pregnan-20-one for the manufacture of a pharmaceutical for the treatment of CNS disorders, the use of 3beta-hydroxy-5alpha-pregnan-20-one for the manufacture of a pharmaceutical for the treatment and prevention of side effects of post-menopausal therapy, and the use of 3beta-hydroxy-5alpha-pregnan-20-one for the manufacture of a pharmaceutical for the treatment and prevention of side effects of oral contraceptives.

In general, the present invention encompasses the use of 3beta-hydroxy-5alpha-pregnan-20-one for the manufacture of a pharmaceutical for the treatment or prevention of any one of the following disorders: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, Alzheimer's dementia, menstrual cycle linked difficulties in concentration, menstrual cycle linked sleep disorders and tiredness.

EXAMPLES

The present invention is based on experiments in vivo, performed to confirm the blocking effect of 3beta-hydroxy-5alpha-pregnan-20-one on 3alpha-hydroxy-5alpha-pregnan-20-one in a preliminary study. 3alpha-hydroxy-5alpha-pregnan-20-one dissolved in 20% cyclodextrin was given to male Sprague-Dawley rats in an i.v. infusion dose rate of close to 3.0 mg/kg/min. This is the optimal dose rate for 3alpha-hydroxy-5alpha-pregnan-20-one. 3alpha-hydroxy-5alpha-pregnan-20-one and 3beta-hydroxy-5alpha-pregnan-20-one were dissolved, 50/50%, in water solution containing cyclodextrin. The control solution only contained 3alpha-hydroxy-5alpha-pregnan-20-one. The amount of 3alpha-hydroxy-5alpha-pregnan-20-one needed to obtain silent second, the anaesthesia criteria, was 21% higher with the combined solution compared to 3alpha-hydroxy-5alpha-pregnan-20-one alone, showing an interaction between 3alpha-hydroxy-5alpha-pregnan-20-one and 3beta-hydroxy-5alpha-pregnan-20-one in vivo. There was no overlap between the effect of the combined solution and control solution of 3alpha-hydroxy-5alpha-pregnan-20-one.

In another preliminary study, the hippocampus slice model in the female rat of the luteal phase was used. This corresponds to the phase in humans when most of CNS effects are noticed in women with epilepsy and premenstrual syndrome.

In the hippocampus slice in vitro model the effect of steroids on an electrical signal over the synapse in the area CA1 was investigated. The stimulation is on one side of the synapse and a measurement of the response is made on the other side. A small droplet containing the steroid can be placed on top of the synapse and thus influence the synaptic transmission. Secondly a steroid can also be dissolved in the nutrient fluid perfusing the hippocampous slice. The steroid in the perfusion will influence the whole slice including the synapse under investigation.

The experiments showed an inhibition of the signal transmitted over the synapse with 3alpha-hydroxy-5alpha-pregnan-20-one and 3alpha-hydroxy-5beta-pregnan-20-one. This inhibition can be blocked by adding 3beta-hydroxy-5alpha-pregnan-20-one in an equimolar dose which is in the nM range. By itself 3beta-hydroxy-5alpha-pregnan-20-one has no effect on signal transmission over the synapse investigation up to micromolar range. This latter finding is similar to results found by several other groups.

3beta-hydroxy-5beta-pregnan-20-one had no blocking effect on either 3alpha-hydroxy-5alpha-pregnan-20-one or 3alpha-hydroxy-5beta-pregnan-20-one. Another similar steroid 3beta-hydroxy-pregnenolone has no blocking effect on the effect of 3alpha-hydroxy-5alpha-pregnan-20-one or 3alpha-hydroxy-5beta-pregnan-20-one. Pregnenolone sulphate which also has a similar structure, and which has been discussed as a blocking substance could neither block the effect of 3alpha-hydroxy-5alpha-pregnan-20-one or 3alpha-hydroxy-5beta-pregnan-20-one. Pregnenolone sulphate had instead a similar effect as 3alpha-hydroxy-5alpha-pregnan-20-one and 3alpha-hydroxy-5beta-pregnan-20-one in low nM concentrations but was excitatory in high micromolar concentrations.

The same blocking effect of 3beta-hydroxy-5alpha-pregnan-20-one was obtained when it was perfused to the whole hippocampus slice and when the response of the CA1 neurons were stimulated with 3alpha-hydroxy-5alpha-pregnan-20-one.

Figure 3:
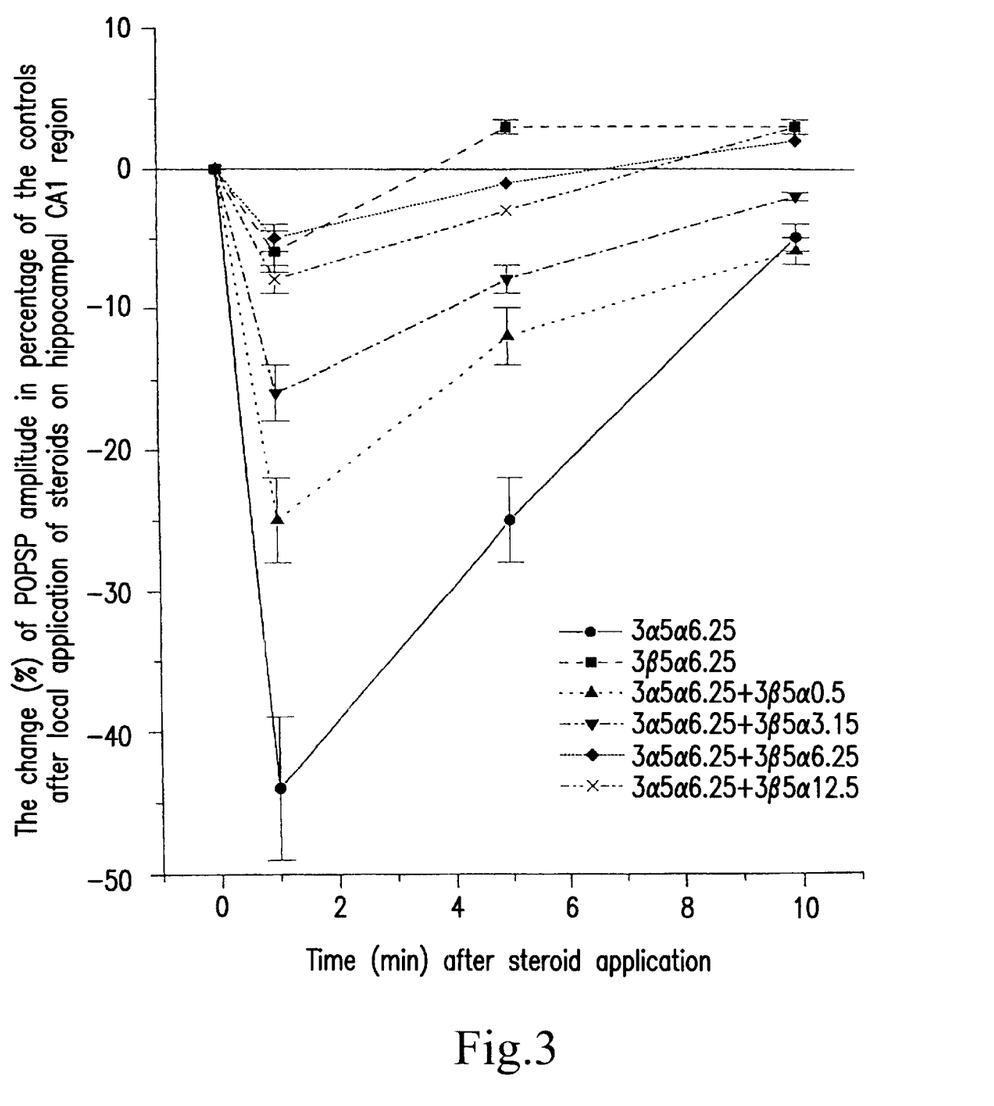
FIG. 3 shows in the effect of local application of the anaesthetic steroid and GABA-A receptor modulator 3alpha-hydroxy-5alpha-pregnan-20-one on the amplitude of the induced population spike (POPSP) in slices from hippocampal CAI region.
Figure 4:
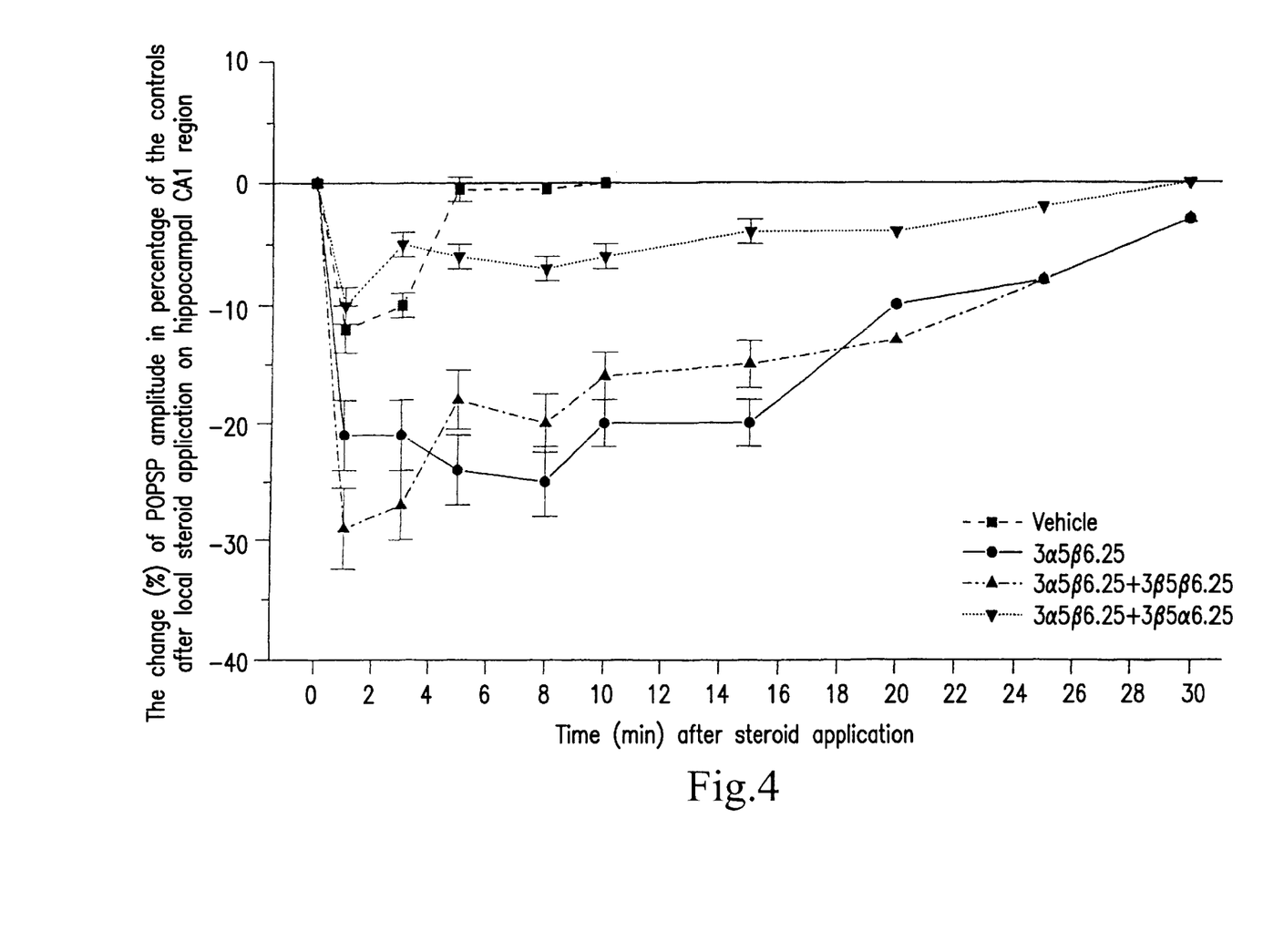
FIG. 4 shows the effect of the vehicle and the effect of local application of another anaesthetic steroid, 3alpha-hydroxy-5beta-pregnan-20-one.

FIG. 3 thus shows the effect of local application of the anaesthetic steroid and GABA-A receptor modulator 3alpha-hydroxy-5alpha-pregnan-20-one on the amplitude of the induced population spike (POPSP) in slices from hippocampal CA1 region. It can be noted that 3alpha-hydroxy-5alpha-pregnan-20-one reduces the amplitude spike with 45%. 3beta-hydroxy-5alpha-pregnan-20-one alone has no effect by itself. The effect noted is not different from the effect of the vehicle which is seen in FIG. 4. It can also be noticed that 3beta-hydroxy-5alpha-pregnan-20-one will decrease the effect of 3alpha-hydroxy-5alpha-pregnan-20-one in a dose dependent manner when they are given simultaneously, up to the equimolar dosage, where the effect of 3alpha-hydroxy-5alpha-pregnan-20-one is totally inhibited.

FIG. 4 shows the effect of the vehicle and the effect of local application of another anaesthetic steroid, 3alpha-hydroxy-5beta-pregnan-20-one. This steroid also inhibits the amplitude of the POPSP and shows that 3beta-hydroxy-5alpha-pregnan-20-one can inhibit the effect of 3alpha-hydroxy-5beta-pregnan-20-one as well. 3beta-hydroxy-5beta-pregnan-20-one, however, had no blocking effect.

Figure 5:
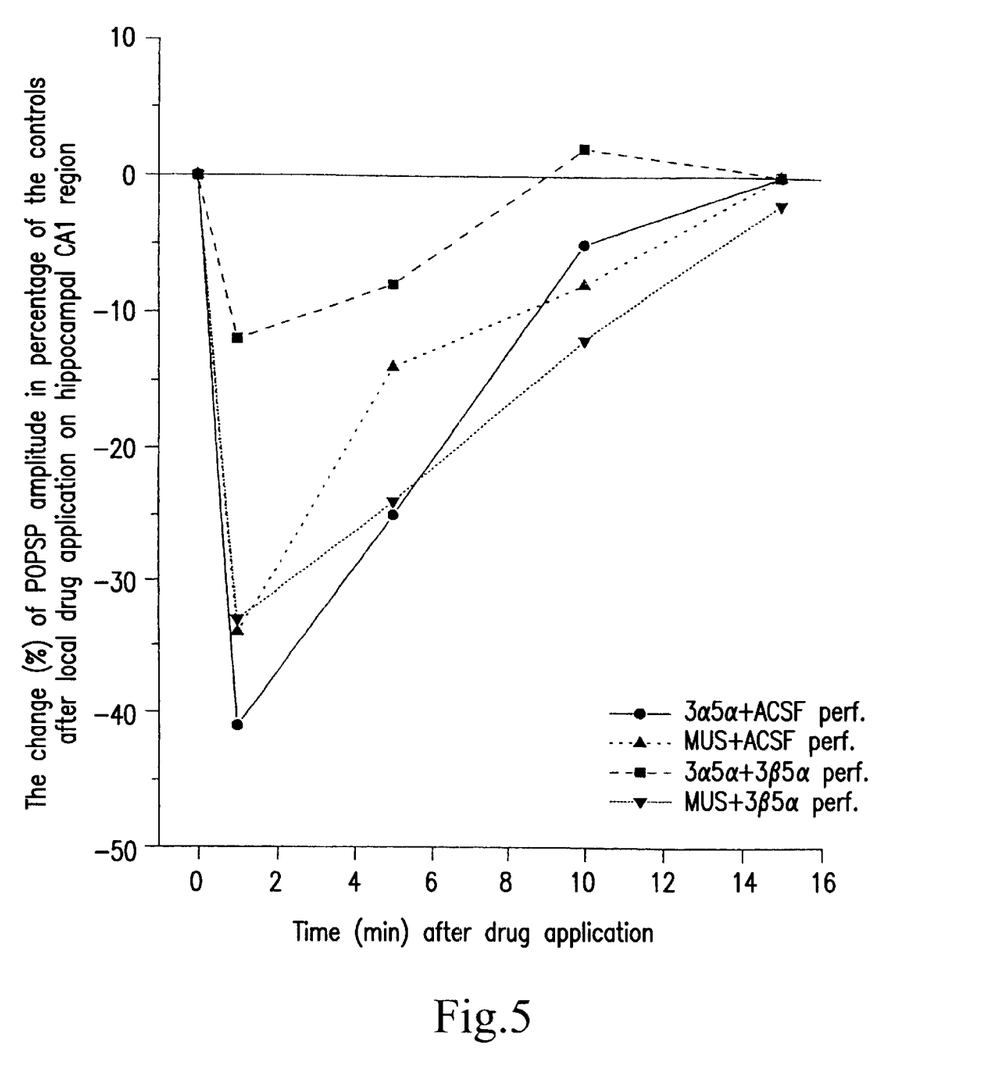
FIG. 5 shows the effect of 3alpha-hydroxy-5alpha-pregnan-20-one together with Muscimol (an agonist to the GABA) on the amplitude of the induced population spike (POPSP) in slices from the hippocampal CAI region.

In FIG. 5 is shown, that 3beta-hydroxy-5alpha-pregnan-20-one does not interact with Muscimol (an agonist to GABA) on the GABA-A receptor indicating that the 3beta-hydroxy-5alpha-pregnan-20-one is not acting via the binding site of GABA and Muscimol.

In further studies, performed after the priority date, the present invention was tested in in vivo experiments in which the blocking effect of 3beta-hydroxy-5alpha-pregnan-20-one was assessed by investigating the dosage of 3alpha-hydroxy-5alpha-pregnan-20-one and 3alpha-hydroxy-5beta-pregnan-20-one needed to induce a deep anaesthesia in the presence of increasing amounts of 3beta-hydroxy-5alpha-pregnan-20-one. An EEG-threshold method for deep anaesthesia was used. The method is developed to determine the sensitivity in the central nervous system (CNS) to the depressant drugs, mainly intravenous anaesthetic agents. Drugs are administered into the tail vein by continuous intravenous infusion while an Electro-Encephalo-Gram (EEG) is recorded. The infusion was immediately stopped and infusion time recorded, when the first burst of EEG suppression for one second or more is noted, the threshold criterion for a deep anaethesia, the "silent second" (SS). The appearance of SS is considered as a deeper anaesthesia state than the loss of righting reflex. The threshold dose (mg/kg) is calculated by multiplying the time to obtain SS with the dose rate (mg/kg/min). The threshold doses of the tested drug indicates its relative anaesthetic potency. The threshold doses are also related to CNS excitability. An increase or decrease in CNS excitability can be measured by a change in threshold doses of anesthetics. The dose rates which give the lowest threshold dose is considered as the optimal dose rate. The optimal dose rate and anaesthetic threshold dosage for 3alpha-hydroxy-5alpha-pregnan-20-one and 3alpha-hydroxy-5alpha-pregnan-20-one has been determined at several times and the optimal dose rate is close to 3.0 mg/kg/min for both 3alpha-hydroxy-5alpha-pregnan-20-one and 3alpha-hydroxy-5beta-pregnan-20-one. The anaesthetic threshold dosage is for 3alpha-hydroxy-5alpha-pregnan-20-one between 6.5 to 8.0 mg/kg and for 3alpha-hydroxy-5beta-pregnan-20-one between 9 to 11 mg/kg depending on the age of the rats and the solvent used.

Figure 1:
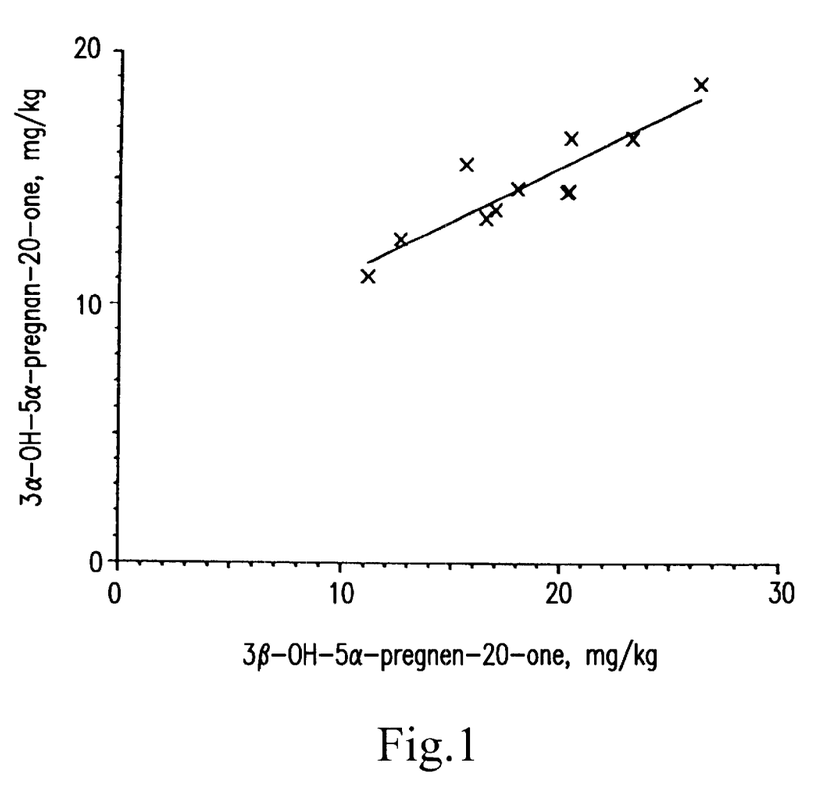
FIG. 1 shows the dosage of 3alpha-hydroxy-5alpha-pregnan-20-one (mg/kg, Y-axis) needed to reach the "silent second" threshold criterion for deep anaesthesia at increasing dosages of 3beta-hydroxy-5beta-pregnan-20-one (mg/kg, X-axis)
Figure 2:
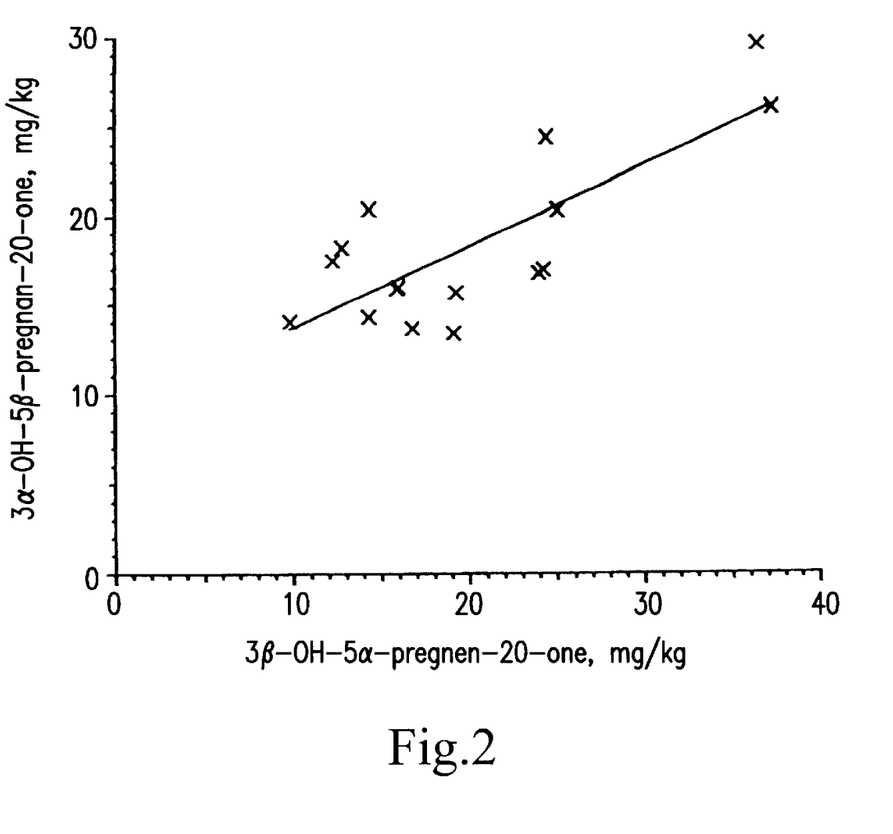
FIG. 2 shows the dosage of 3alpha-hydroxy-5beta-pregnan-20-one (mg/kg, Y-axis) needed to reach the "silent second" threshold criterion for deep anaesthesia at increasing dosages of 3beta-hydroxy-5alpha-pregnan-20-one (mg/kg, X-axis) given simultaneously in an intravenous infusion.

3alpha-hydroxy-5alpha-pregnan-20-one and 3beta-hydroxy-5beta-pregnan-20-one dissolved in 20% cyclodextrin were given to Sprague-Dawley rats in an intravenous infusion at the optimal dose rate. 3beta-hydroxy-5alpha-pregnan-20-one was also dissolved in a 20% cyclodextrin solution and given simultaneously in a dosage 100%, 123% and 143% of the 3alpha-hydroxy-5alpha-pregnan-20-one dosage (n=11) and 70%, 100%, 123% and 143% of the 3alpha-hydroxy-5beta-pregnan-20-one dosage (n=16). The addition of 3beta-hydroxy-5alpha-pregnan-20-one to the 3alpha-hydroxy-5alpha-pregnan-20-one and 3alpha-hydroxy-5beta-pregnan-20-one infusion decreased the anaesthetic potency of 3alpha-hydroxy-5alpha-pregnan-20-one and 3alpha-hydroxy-5beta-pregnan-20-one in a dose dependent fashion. The correlation between the dosage 3beta-hydroxy-5alpha-pregnan-20-one given and the dosage of 3alpha-hydroxy-5alpha-pregnan-20-one and 3alpha-hydroxy-5beta-pregnan-20-one needed to obtain the criterion of SS is highly significant (FIG. 1 and FIG. 2). By itself 3beta-hydroxy-5alpha-pregnan-20-one has no effect on CNS activities, a result found by several groups and described in earlier reports.

FIG. 1 shows the dosage of 3alpha-hydroxy-5alpha-pregnan-20-one (mg/kg, Y-axis) needed to reach the criterion of SS at increasing dosages of 3beta-hydroxy-5alpha-pregnan-20-one (mg/kg, X-axis) given simultaneously in an intravenous infusion. Note that clear linear relationship between the dosages of 3beta-hydroxy-5alpha-pregnan-20-one and 3alpha-hydroxy-5alpha-pregnan-20-one. Correlation coefficient r=0.90; p<0.001, df=9, with the regression line 3alpha-hydroxy-5alpha-pregnan-20-one=0.43×3beta-hydroxy-5alpha-pregnan-20-one+6.9, the slope of the line is significantly different (p<0.001) from 0, that is the x-axis.

FIG. 2 shows the dosage of 3alpha-hydroxy-5beta-pregnan-20-one (mg/kg, Y-axis) needed to reach the criterion of SS at increasing dosages of 3beta-hydroxy-5alpha-pregnan-20-one (mg/kg, X-axis) given simultaneously in an intravenous infusion. Note the clear linear relationship between the dosages of 3beta-hydroxy-5alpha-pregnan-20-one and 3alpha-hydroxy-5beta-pregnan-20-one. Correlation coefficient r=0.78; P<0.001, df=14, with the regression line 3alpha-hydroxy-5beta-pregnan-20-one=0.46×3beta-hydroxy-5alpha-pregnan-20-one+9.1, the slope of the line is significantly different (p<0.001) from 0 that is the x-axis.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A method of treating CNS disorders that are induced by endogenously produced 3alpha-hydroxy-5alpha steroids or 3alpha-hydroxy-5beta steroids, in human patients which comprises administering to a patient in need thereof of an amount of 3beta-hydroxy-5alpha-pregnan-20-one which is therapeutically effective by blocking the action of 3alpha-hydroxy-5alpha steroids or 3alpha-hydroxy-5beta steroids on the central nervous system.

2. A method of treating CNS disorders that are induced by tolerance development against endogenously produced 3alpha-hydroxy-5alpha or 3alpha-hydroxy-5beta steroids, in human patients which comprises administering to a patient in need thereof an amount of 3beta-hydroxy-5alpha-pregnan-20-one which is therapeutically effective by blocking the action of 3alpha-hydroxy-5alpha steroids or 3alpha-hydroxy-5beta steroids on the central nervous system.

3. A method of treating CNS disorders that are induced by withdrawal of endogenously produced 3alpha-hydroxy-5alpha steroids or 3alpha-hydroxy-5beta steroids, in human patients which comprises administering to a patient in need thereof an amount of 3beta-hydroxy-5alpha-pregnan-20-one which is therapeutically effective by blocking the action of 3alpha-hydroxy-5alpha steroids or 3alpha-hydroxy-5beta steroids on the central nervous system.

4. A method of treating a CNS disorder induced by endogenously produced 3alpha-hydroxy-5alpha steroids or 3beta-hydroxy-5beta steroids and selected from the group consisting of epilepsy, depression, stress-related depression, migraine, tiredness, stress-related tiredness, premenstrual syndrome premenstrual dysphoric disorder, menstrual cycle-linked mood changes, menstrual cycle-linked memory changes, stress-related memory changes, menstrual cycle-linked difficulties in concentration and menstrual cycle-linked sleep disorders and tiredness, in human patients which comprise administering to a patient in need thereof an amount of 3beta-hydroxy-5alpha-pregnan-20-one which is therapeutically effective by blocking the 3alpha-hydroxy-5alpha steroids or 3alpha-hydroxy-5beta steroids.

* * * * *